US009050261B2

(12) United States Patent
Wöhrle et al.

(10) Patent No.: US 9,050,261 B2
(45) Date of Patent: Jun. 9, 2015

(54) COMPOSITIONS COMPRISING FRAGRANCE SUBSTANCES AND COMPRISING CETYL NONANOATE AND/OR STEARYL NONANOATE

(75) Inventors: Ingo Wöhrle, Bremen (DE); Walter Kuhn, Holzminden (DE); Manfred Meier, Fürstenberg (DE); Gerhard Schmaus, Höxter-Bosseborn (DE)

(73) Assignee: SYMRISE AG, Holzminden (DE)

( * ) Notice: Subject to any disclaimer, the term of this patent is extended or adjusted under 35 U.S.C. 154(b) by 1199 days.

(21) Appl. No.: 12/907,706

(22) Filed: Oct. 19, 2010

(65) Prior Publication Data
US 2011/0091404 A1    Apr. 21, 2011

(30) Foreign Application Priority Data
Oct. 19, 2009 (EP) .................................. 09173453

(51) Int. Cl.
*A61K 8/37* (2006.01)
*A61Q 13/00* (2006.01)

(52) U.S. Cl.
CPC .. *A61K 8/37* (2013.01); *A61Q 13/00* (2013.01)

(58) Field of Classification Search
CPC ...... A61Q 13/00; A61K 8/37; A61K 2800/77
See application file for complete search history.

(56) References Cited

U.S. PATENT DOCUMENTS

| 3,939,099 A | 2/1976 | Tusa et al. |
| 5,571,503 A * | 11/1996 | Mausner ........................ 424/59 |
| 6,210,688 B1 | 4/2001 | Quayle |
| 6,737,396 B2 | 5/2004 | Margot et al. |
| 2006/0029624 A1 * | 2/2006 | Banowski et al. ............ 424/401 |
| 2006/0089413 A1 | 4/2006 | Schmaus et al. |
| 2008/0070825 A1 | 3/2008 | Bertram et al. |

FOREIGN PATENT DOCUMENTS

| EP | 0 181 401 A1 | 5/1986 |
| EP | 0 857 481 A1 | 8/1998 |
| EP | 1 872 831 A1 | 1/2008 |
| FR | 2 747 306 A1 | 10/1997 |
| WO | WO-0176572 A2 | 10/2001 |
| WO | WO-02/15686 A1 | 2/2002 |
| WO | WO-2004/098556 A1 | 11/2004 |
| WO | WO-2005107692 A1 | 11/2005 |
| WO | WO-2005123101 A1 | 12/2005 |
| WO | WO-2006015954 A1 | 2/2006 |
| WO | WO-2006045760 A1 | 5/2006 |
| WO | WO-2006053912 A1 | 5/2006 |
| WO | WO-2007042472 A1 | 4/2007 |
| WO | WO-2007/060256 A2 | 5/2007 |
| WO | WO-2007110415 A2 | 10/2007 |
| WO | WO-2007/128723 A1 | 11/2007 |
| WO | WO-2008046676 A1 | 4/2008 |
| WO | WO-2008046791 A1 | 4/2008 |
| WO | WO-2008046795 A1 | 4/2008 |

OTHER PUBLICATIONS

Bauer et al. (Cyclic Terpenes. In Common Fragrance and Flavor Materials: Preparation, Properties and Uses Third Completely Revised Edition. Wiley-VCH:NY;1997, 71-72).*
Gaunt et al. Food and Cosmetics Toxicology 1971, 9(3), abstract).*
H. Surburg et al., "Common Fragrance and Flavor Materials," $5_{th}$. Ed., Wiley-VCH, Weinheim, 2006.
I. Watanabe et al., Ester Compounds of Bulgarian Rose Concrete (*Rosa damascena* Mill.), $7_{th}$ Int. Congr. Essent. Oils, Kyoto, Oct. 7-11, 1977, vol. 7, pp. 461-466, 1979.
J.-L. Boevé et al., "The secretion of the ventral glands in *Cladius, Priophorus* and *Trichiocampus* sawfly larvae," Biochemical Systematics and Ecology 28(9), (2000), pp. 857-864.
C. Gancet et al.,"Hydrolyse et synthése de liaison ester par la lipase d'un mycélium dévitalisé de *Rhizopus arrhizus* en milieu non aqueux," Revue Française des Corps Gras 1986, 33(11), pp. 423-430.
F.W. Koontz et al., "The Sternal Gland of the Rufous Elephant-Shrew, *Elephantulus rufescens* (Macroscelidea, Mammalia)," *Advances in Chemical Signals in Vertebrates*, Kluwer Academic/Plenum Publishers, New York, N. Y., 1999, pp. 163-171.
ip.com, "Perfumed Cosmetic Composition with Long Lasting Fragrance," #000033581D, (published Jan. 2005).

* cited by examiner

*Primary Examiner* — Abigail Fisher
*Assistant Examiner* — Jessica Kassa
(74) *Attorney, Agent, or Firm* — Novak Druce Connolly Bove + Quigg LLP

(57) ABSTRACT

The invention relates to the use of n-hexadecyl n-nonanoate (CAS number 72934-15-7, hereafter cetyl nonanoate) and n-octadecyl n-nonanoate (CAS number 107647-13-2, hereafter stearyl nonanoate) and to the mixtures thereof (CAS number 878027-13-5) as fixatives for fragrance substances. The invention also relates to specific compositions comprising (A) cetyl nonanoate and/or stearyl nonanoate as well as (B) one or more fragrance substances. The invention also relates to a process for the preparation of such compositions as well as to (cosmetic) products comprising a composition according to the invention. The invention further relates to a process for imparting, intensifying or modifying an odor on (human) skin. A particular aspect of the present invention relates to the improvement in the adhesive strength of a composition according to the invention on (human) skin and/or (human) hair.

13 Claims, No Drawings

COMPOSITIONS COMPRISING FRAGRANCE SUBSTANCES AND COMPRISING CETYL NONANOATE AND/OR STEARYL NONANOATE

CROSS-REFERENCE TO RELATED APPLICATIONS

This application claims priority under 35 U.S.C. §119(a) to European Application No. 09 173 453.3, filed Oct. 19, 2009, the entire contents of which is hereby incorporated by reference.

The invention relates to the use of n-hexadecyl n-nonanoate (CAS number 72934-15-7, hereafter cetyl nonanoate) and n-octadecyl n-nonanoate (CAS number 107647-13-2, hereafter stearyl nonanoate) and to the mixtures thereof (CAS number 878027-13-5) as fixatives for fragrance substances. The invention also relates to specific compositions comprising (A) cetyl nonanoate and/or stearyl nonanoate as well as (B) one or more fragrance substances. The invention also relates to a process for the preparation of such compositions as well as to (cosmetic) products comprising a composition according to the invention. The invention further relates to a process for imparting, intensifying or modifying an odor on (human) skin. A particular aspect of the present invention relates to the improvement in the adhesive strength of a composition according to the invention on (human) skin and/or (human) hair.

In the field of fragrance substances and perfumery, it is generally known that when fragrance substance compositions are applied to the skin, the fragrance substances, in particular the readily volatile top note, fade(s) away due to the evaporation of diluents or solvents, while the more difficulty volatile notes have an excellent adhesion to the skin and are released from the skin over a long period of time and thus the odor thereof is detected for a relatively long time. Due to the faster evaporation of the top note, a significant change in the odor profile of fragrance substance compositions applied to the skin thus takes place over the course of time. A similar effect occurs when fragrance substance compositions are applied to (human) hair. In this respect, it should be considered that the described disadvantageous effect is perceived as being a problem particularly when a fragrance substance composition (fragrance substance mixture) is used as a leave-on product, i.e. is to remain on the skin and/or hair in order to be released therefrom over a relatively long period of time.

For the purposes of the present text, the terms adhesion, adhesive strength, adhesion ability and affinity are understood as meaning the adhesion of a fragrance substance to the skin and hair, in particular the adhesion to human skin (excluding the (oral) mucous membrane). Thus, although the present invention also relates to the (oral) mucous membrane in respect of the application of fragrance substance compositions, it should be established that the significance of the present invention is of much greater relevance in respect of the aspects of skin (excluding (oral) mucous membrane) and/or hair (in particular human hair), since when a fragrance substance composition is applied to the (oral) mucous membrane, the negative evaporation effect is routinely superimposed and dominated by washing-away effects (in the area of the oral mucous membrane furthered, for example, by the influence of saliva).

In perfumery practice, numerous attempts have already been made to prolong the adhesion ability or the perceptibility of fragrance substance compositions, in particular on (human) skin and to thus achieve a certain olfactory, temporal "profile stability".

A fixative increases the adhesive strength of fragrance substances, for example by lowering their vapor pressure. In this respect, the term "fixatives" is understood as meaning substances which allow a time-delayed release of the perfume oil components, for example on the skin and/or hair and thus ensure a longer lasting fragrance impression.

Fixatives which are particularly suitable in this respect are those which are odorless or which have a very slight inherent odor so that they do not alter the odor impression of fragrance substances, fragrance substance mixtures and perfume oils.

The use of fixatives has been described many times, i.e. the use of individual substances or combinations of (fragrance) substances which are added to more readily volatile fragrance substances or fragrance substance mixtures in order to reduce the evaporation rate thereof (cf. U.S. Pat. No. 6,737,396).

IP.COM #000033581 D (published January 2005), describes the use of hydroxyalkyl urea derivatives, particularly hydroxyethyl urea, as a result of which the adhesion characteristics of perfumes in cosmetic applications, in particular aqueous-ethanol formulations, on the skin and hair are prolonged.

U.S. Pat. No. 3,939,099 describes the use of film-formers which are dissolved in a water/ethanol mixture and are miscible with fragrance substance (mixtures). Ionic and non-ionic derivatives of water-soluble polymers are mentioned as examples, for example polyvinyl pyrrolidone derivatives, quaternary polyvinyl pyrrolidones having molecular weights ranging from 50000 to 1000000, cationic cellulose derivatives and the like. When ethanol evaporates, a film is formed on the skin in which the fragrance substances are stored.

U.S. Pat. No. 6,210,688 describes the formation and use of an odorless polymer film on the skin (based on vinylether copolymers, polyacrylates, methacrylates, polyesters, polyfluorohydrocarbons, polysaccharides), to which a perfume is then applied. It is stated that this will prevent "reactions" with the skin.

FR 2 747 306 describes the use of polymeric hydrocarbons (polyethylenes having molecular weights of between 3000 and 30000). Since these polymers are insoluble in ethanol/water, a corresponding product, for example Eau de Cologne, EdT or an Eau de Parfum, is cloudy.

WO 2004/098556 describes a novel sprayable, clear perfume formulation which is characterized by an increased surface tension or reduced contact surface after application which is achieved using an effective quantity of a polymer. Due to the smaller contact surface, after the ethanol has evaporated the remaining perfume oil is concentrated over a smaller surface, from which the fragrance substances evaporate relatively slowly.

Film formers and/or polymers suffer from the disadvantage that they not only reduce the evaporation rate of the top notes, but also that of all the other more difficultly volatile fragrance substances, thereby significantly reducing the overall intensity. Furthermore, film formers can produce an unpleasant tacky or tightening feeling on the skin.

EP 0 181 401 and EP 0 857 481 describe gel-type perfume preparations in which the diffusion and thus also the evaporation of fragrance substances is reduced. However, the proposed gel formation is particularly unsuitable for some application areas, for example fine perfumery or products in the form of lotions or sprays, since the gel-type preparations described there are too viscous.

EP 1 872 831 describes specific ethanolic fragrance substance compositions comprising deliquescent substances for imparting, intensifying or modifying an odor, in particular for improving the adhesive strength of ethanolic fragrance substance compositions on (human) skin and/or (human) hair.

The desired fixatives should satisfy the above requirements and should be effectively miscible with as many current (perfumery) fragrance substances and perfume oils as possible and furthermore should be able to be incorporated into a large number of cosmetic formulations.

Therefore, the primary object of the present invention was to provide a (alternative) fragrance substance composition in which the fragrance substances which are used, preferably fragrance substances which form the top note and/or the base note of a fragrance, have a long adhesion (adhesive strength) (prolonged adhesion compared to conventional fragrance substance compositions) in particular on (human) skin (this means skin excluding mucous membrane) and/or on (human) hair. In this respect, the disadvantages described above of previous fragrance substance compositions should be avoided as far as possible.

The primary object is achieved according to the invention by a composition comprising (or consisting of):
(A) cetyl nonanoate and/or stearyl nonanoate,
and
(B) one or more fragrance substances, preferably a fragrance substance mixture comprising 2, 3, 4, 5, 6, 7, 8, 9, 10 or more fragrance substances,
wherein component (A) is comprised in a fixing quantity for the one, more or all the fragrance substances of component (B), wherein the mass ratio of component (A) to the total mass of component (B) is preferably in the range of from 1:20 to 200:1, preferably in the range of from 1:12 to 100:1, more preferably in the range of from 1:6 to 50:1, particularly preferably in the range of from 1:5 to 33:1 and most particularly preferably in the range of from 1:2 to 25:1.

The phrase "a fixing quantity of component (A)" is understood as meaning a quantity of component (A) which is sufficient to fix one, more or all the fragrance substances of component (B).

Surprisingly, the compositions according to the invention show a fixing of the one, more or all the fragrance substances of component (B) by component (A), in particular when the mass ratios which have been described as being preferred are adjusted. A fixing quantity of component (A) which acts as fixative for one, more or all the fragrance substances of component (B) produces an improved and prolonged adhesion (adhesive strength) of component (B), in particular on (human) skin and/or (human) hair. This also applies to cosmetic products according to the invention which preferably comprise a sensorially (olfactorily) effective quantity of a composition according to the invention.

In the publication on the 7$^{th}$ Int. Congr. Essent. Oils, Kyoto 1977, October 7-11, Volume 7, 461-466 (1979), Bulgarian rose concrete (*Rosa damascene* Mill.) is investigated analytically. In addition to numerous fragrance substances, numerous ester components were identified and included among these was also cetyl nonanoate as an unquantified trace component. Stearyl nonanoate was not found. In an embodiment, a composition according to the invention is not a Bulgarian rose concrete, particularly not a Bulgarian rose concrete as described in this document. In a further preferred embodiment, a composition according to the invention or a cosmetic product according to the invention does not comprise any Bulgarian rose concrete. In a further preferred embodiment, a composition according to the invention or a cosmetic product according to the invention does not comprise *Rosa damascene* concrete.

According to Biochemical Systematics and Ecology 2000, 28(9), 857-864, cetyl nonanoate was found in a proportion of 1 GC % in the gland extract of the wasp species *Trichiocampus grandis* which comprises, inter alia, traces of the fragrance substance (Z)-3-octenal. An extract of this type is not the subject-matter of the present invention. In a preferred embodiment, a composition according to the invention is not a gland extract of *Trichiocampus grandis*, in particular not a wasp extract as described in the above document. In preferred embodiments, a composition according to the invention is either free from (Z)-3-octenal (which is not a perfumery fragrance substance according to the definition provided below) or it comprises, in addition to (Z)-3-octenal at least one further fragrance substance, preferably two, three, four, five or more further fragrance substances, preferably perfumery fragrance substances (as defined below).

In Revue Française des Corps Gras 1986, 33(11), 423-430, the lipase activity of the mycelium of the (pathogenic) fungus *Rhizopus arrhizus* is investigated. This document describes, inter alia, the esterification of a C18 alcohol (possibly stearyl alcohol) with a C9 carboxylic acid (possibly n-nonanoic acid) in methyl-tert.-butyl ether (MTBE) in the presence of the mycelia of *Rhizopus arrhizus* and a molecular sieve. It is not known whether *Rhizopus arrhizus* comprises any fragrance substances. A mixture as described in Revue Française des Corps Gras 1986, 33(11), 423-430 is not the subject matter of the present invention. As a precaution, in preferred embodiments, a composition according to the invention is free from MTBE, molecular sieve and/or mycelia of *Rhizopus arrhizus*.

In the publication on the 8$^{th}$ International Symposium on Chemical Signals in Vertebrates, Ithaca, N.Y., Jul. 20-25, 1997, published in 1999 in Advances in Chemical Signals in Vertebrates, 1999, 163-171, Kluwer Academic/Plenum Publishers, New York, N.Y., it is stated that cetyl nonanoate and stearyl nonanoate in a gland secretion of the reddish brown rufous elephant shrew *Elephantus rufescens* which also comprises, inter alia, fragrance substances such as nonanal. No information concerning quantities or proportions of the glandular secretion components is provided. A secretion of this type is not the subject matter of the present invention. Accordingly, a composition according to the invention is not a glandular secretion of *Elephantus rufescens*, and in particular not a glandular secretion as described in the above document.

Component (A)

Cetyl nonanoate (hexadecyl nonanoate; CAS number 72934-15-7; following formula I) and stearyl nonanoate (octadecyl nonanoate; CAS number 107647-13-2, following formula II) correspond to the following structural formulae:

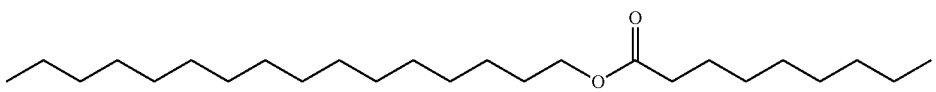

Formula (I)

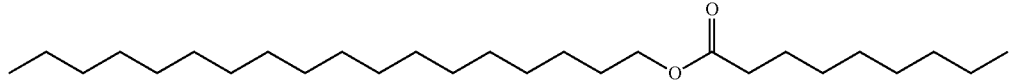

Formula (II)

Cetyl nonanoate and stearyl nonanoate as well as mixtures thereof (CAS number 878027-13-5) can be prepared by the conversion of cetyl alcohol and/or stearyl alcohol, for example using conventional chemical or biotechnological esterification processes. Furthermore, they are commercially available, as are mixtures thereof.

Compositions according to the invention preferably comprise cetyl nonanoate and stearyl nonanoate. The mass ratio of cetyl nonanoate to stearyl nonanoate is especially in the range of from 1:9 to 9:1, preferably in the range of from 2:8 to 8:2, more preferably in the range of from 3:7 to 7:3, since such compositions exhibit improved olfactory effects in the sense described above.

Component (A) of a composition according to the invention is eminently suitable for the object which has been set, since cetyl nonanoate and stearyl nonanoate as well as mixtures thereof have no inherent odor or in any case only a very slight inherent odor. Component (A) is of course not part of component (B).

Furthermore, cetyl nonanoate and stearyl nonanoate as well as in particular the mixtures thereof, preferably in the above-mentioned weight ratios, have a melting range which is close to human skin temperature, so that such mixtures provide a pleasant feeling on the skin, as a result of which compositions according to the invention are eminently suitable for application to (human) skin and also for incorporation and as part of cosmetic (topical) products.

Component (B)

Examples of fragrance substances of component (B) as well as the (preferred) components (B*), (B) (i) and (B) (ii) are known to a person skilled in the art and can be found, for example, in S. Arctander, Perfume and Flavor Materials, Vol. I and II, Montclair, N.J., 1969, private publishing house or H. Surburg, J. Panten, "Common Fragrance and Flavor Materials", 5$^{th}$. Ed., Wiley-VCH, Weinheim 2006.

Component (B) is preferably a fragrance substance mixture, preferably a fragrance substance mixture comprising 3, 4, 5, 6, 7, 8, 9, 10 or more fragrance substances, more preferably perfumery fragrance substances, in particular a perfume oil.

Preferred fragrance substances of component (B) are perfumery fragrance substances which are in turn preferably selected from the group (B*) consisting of the group of individual compounds disclosed as fragrance substances according to S. Arctander, Perfume and Flavor Materials, Vol. I and II, Montclair, N.J., 1969, private publishing house ("Arctander"), H. Surburg, J. Panten, "Common Fragrance and Flavor Materials", 5$^{th}$. Ed., Wiley-VCH, Weinheim 2006 ("Surburg"), and the individual compounds described as fragrance substances within the scope of the present text.

If, in a particular case, there should be lack of agreement or a contradiction between these three references, the present text will take precedence over "Arctander" and "Surburg". If, in a particular case, there should be lack of agreement or a contradiction between "Surburg" and "Arctander", "Surburg" will take precedence over "Arctander".

In a preferred embodiment, the present invention relates to a composition comprising (or consisting of):

(A) cetyl nonanoate and/or stearyl nonanoate, and (B) one or more fragrance substances of group (B*), as defined above, preferably a fragrance mixture comprising 2, 3, 4, 5, 6, 7, 8, 9, 10 or more fragrance substances of group (B*), wherein the mass ratio of component (A) to the total mass of component (B*) is in the range of from 1:20 to 200:1, preferably in the range of from 1:12 to 100:1, more preferably in the range of from 1:6 to 50:1, particularly preferably in the range of from 1:5 to 33:1 and most particularly preferably in the range of from 1:2 to 25:1.

Further preferred compositions according to the invention are those in which component (B), preferably component (B*), comprises (B) (i) one or more fragrance substances having a molecular weight in the range of from 100 g/mol to 175 g/mol (top note), preferably having a molecular weight in the range of from 110 g/mol to 160 g/mol, preferably in the range of from 115 g/mol to 160 g/mol, particularly preferably in the range of from 120 g/mol to 155 g/mol, and/or (B) (ii) one, two, three, four, five or more fragrance substances having a molecular weight of greater than or equal to 190 g/mol (base note), preferably having a molecular weight in the range of from 190 g/mol to 300 g/mol, preferably having a molecular weight in the range of from 195 g/mol to 290 g/mol and particularly preferably in the range of from 200 to 275 g/mol.

In a preferred embodiment, a composition according to the invention comprises at least 2, 3, 4, 5 or more fragrance substances of component (B) (i), and/or at least 2, 3, 4, 5 or more fragrance substances of component (B) (ii).

Compositions according to the invention which comprise one or more fragrance substances (described as being preferred) of component (B) (i), in particular in the proportions stated in the following, and one or more fragrance substances of component (B) (ii), also exhibit an olfactory harmonization and rounding off, thereby producing a more elegant odor impression which is thus more valuable in terms of odor. This applies in particular to musk fragrance substances and to further base notes of component (B) (ii), described in the following as being preferred, in particular in the proportions stated below.

The (preferred) fragrance substances of components (B), (B*), (B) (i) and (B) (ii) can, if appropriate, be present in the form of their respective diastereomers, enantiomers and/or double bond isomers. Thus, they can be present as (E)/(Z) isomers, as any mixture of the enantiomers, in particular as a racemate, or also as any mixture of the corresponding diastereomers.

Component (B) (i)

The fragrance substances of component (B) (i) are to be considered as top notes of a composition according to the invention or of a cosmetic product according to the invention.

The top note determines the initial odor of a fragrance substance mixture or of a perfume.

The molecular weight of the fragrance substances of component (B) (i) is in the range of from 100 g/mol to 175 g/mol (top note), preferably in the range of from 110 g/mol to 160 g/mol, preferably in the range of from 115 g/mol to 160 g/mol and particularly preferably in the range of from 120 g/mol to 155 g/mol.

Component (B) (i) of a composition according to the invention (in particular in one of the embodiments characterized as being preferred) preferably comprises one or more fragrance substances from the group consisting of:
n-heptanol, camphor, alpha-pinene, beta-pinene, limonene, 6-methyl-5-hepten-2-one, octanal, eucalyptol (1,8-cineol), rose oxide, 3-hexenol, dihydromyrcenol (2,6-dimethyl-7-octen-2-ol), menthone, isomenthone, 2,6-dimethyl-5-hepten-1-al (melonal), 3-hexenylmethylcarbonate, benzaldehyde, linalool, tetrahydrolinalool, citral, neral, geranial, benzyl alcohol, p-anisaldehyde, menthol, isoamyl acetate, isoamyl butyrate, cis-3-hexenyl acetate, hexyl acetate, butyl butyrate, citronellol, nerol, geraniol, 2-phenylethyl alcohol, methyl benzoate, agrunitrile (3,7-dimethyl-6-octene-1-nitrile) and vanillin.

The following fragrance substances of component (B) (i) are particularly preferred, since they produced a higher retention: n-heptanol, limonene, 6-methyl-5-hepten-2-one, octanal, rose oxide, dihydromyrcenol (2,6-dimethyl-7-octen-2-ol), 2,6-dimethyl-5-hepten-1-al (melonal), 3-hexenylmethyl carbonate, linalool, citral, neral, geranial, p-anisaldehyde, hexyl acetate, citronellol, nerol, geraniol, 2-phenylethyl alcohol, methyl benzoate, agrunitrile (3,7-dimethyl-6-octene-1-nitrile) and vanillin. When the mentioned fragrance substances of group (B) (i) are used, the stated effects are particularly pronounced.

The total quantity of the fragrance substance or substances (described as being preferred) of component (B) (i) (top note) of a composition preferred according to the invention or of a cosmetic product preferred according to the invention is from 5 to 80% by weight, particularly preferably from 10 to 70% by weight, in each case based on the total weight of component (B), preferably based in each case on the total weight of component (B*).

Component (B) (ii)

The fragrance substances of component (B) (ii) are to be considered as base notes of a composition according to the invention or of a cosmetic product according to the invention. The base note determines the after-odor of a fragrance substance mixture or of a perfume oil.

The molecular weight of the fragrance substances of component (B) (ii) is greater than or equal to 190 g/mol, and is preferably in the range of from 190 g/mol to 300 g/mol, more preferably in the range of from 195 g/mol to 290 g/mol and most preferably in the range of from 200 to 275 g/mol.

The effects of the present invention which have been described can be achieved most clearly and in the most pronounced manner using such fragrance substances of component (B) (ii).

Preferred compositions according to the invention are those in which component B) (ii) comprises one, two, three or more fragrance substances, selected from the group consisting of:
musk fragrance substances,
alpha-n-amylcinnamaldehyde (MW=202.30), alpha-iso-amylcinnamaldehyde (MW=202.30), alpha-n-hexylcinnamaldehyde (MW=216.32), alpha-iso-hexylcinnamaldehyde (MW=216.32), benzyl salicylate (MW=228.25), cis-3-hexenylsalicylate (MW=220.27), isoamyl salicylate (MW=208.26), hexyl salicylate (MW=222.28), 2-methyl-3-(4-tert-butylphenyl)propanal (MW=204.31; 2-methyl-3-(4-isopropylphenyl)propanal (MW=190.28, cyclamen aldehyde), 2,3,8,8-tetramethyl-1,2,3,4,5,6,7,8-octahydro-2-naphthalenyl methyl ketone (MW=234.38, Iso E Super®), 1-[1,2,3,4,6,7,8,8a-octahydro-1,2,8,8-tetramethylnaphthalen-2-yl]ethanone (MW=234.38, Iso E Super®), methyl dihydrojasmonate (MW=226.32, Hedione®), linalyl acetate (MW=196.29), ethyl linalyl acetate (MW=210.31), Nerolidol (MW=222.37), Farnesol (MW=222.37), cedryl methyl ether (MW=236.40, Cedramber), cedryl methyl ketone (MW=246.39), cedryl acetate (MW=264.41), (4aR,5R,7aS,9R)-octahydro-2,2,5,8,8,9a-hexamethyl-4H-4-a,9-methanoazuleno(5,6-d) 1,3-dioxole) (MW=278.44, Ambrocenide®), hexahydro-1',1',5',5'-tetramethyl-spiro[1,3-dioxolane, 2,8'(5'H)-[2H-2,4-a]-methanonaphthalene (MW=264.41 ethylene dioxi-3H-isolongifolan, Ysamber® K), 2-methyl-4-(2,2,3-trimethyl-3-cyclopenten-1-yl)butanol (MW=196.34, brahmanol), 5-(2,2,3-trimethyl-3-cyclopenten-1-yl)-3-methylpentan-2-ol (MW=210.36, Sandalore®), 2-ethyl-4-(2,2,3-trimethyl-3-cyclopenten-1-yl)-2-buten-1-ol (MW=208.35, Sandranol®), 3-methyl-5-(2,2,3-trimethyl-3-cyclopenten-1-yl)-4-penten-2-ol (MW=208.35, Ebanol®), 3,3-dimethyl-5-(2,2,3-trimethyl-3-cyclopenten-1-yl)-4-penten-2-ol (MW=222.37, Polysantol®), 3-isocamphylcyclohexanol (MW=236.40, Sandel 80®), 1-(2,2,6-trimethylcyclohexyl)hexan-3-01 (MW=226.41, Timberol®), cyclododecyl methyl ether (MW=198.35, Palisandin), (ethoxymethoxy)cyclododecane (MW=242.41, Boisambrene Forte®), 1-methyl-4-(4-methyl-3-penten-1-yl)-3-cyclohexencarboxaldehyde (MW=206.33, Precyclemone B®), 4-(4-hydroxy-4-methylpentyl)-3-cyclohexenecarboxaldehyde (MW=210.32, Lyral®), 2-methyl-4-(2,2,6-trimethyl-1-cyclohexen-1-yl)-2-butenal (MW=206.33, Boronal), decahydro-beta-naphthyl acetate (MW=196.29), allyl-3-cyclohexylpropionate (MW=196.29), allyl cyclohexyloxy acetate (MW=198.26, Isoananat®), Citraldiethylacetal (MW=226.36), benzyl benzoate (MW=212.25), benzyl cinnamate (MW=238.29), 3a,6,6,9a-tetramethyldodecahydronaphtho[2,1-b]furan (MW=236.40, Ambroxid®), alpha-Iron (MW=206.33), beta-Iron (MW=206.33), alpha-n-methyl ionone (MW=206.33), beta-n-methyl ionone (MW=206.33), alpha-isomethyl ionone (MW=206.33), beta-isomethyl ionone (MW=206.33) and allyl ionone (MW 232.35), 2,3,8,8-tetramethyl-1,2,3,4,5,6,7,8-octahydro-2-naphthalenyl methyl ketone (MW=234.38), 1-[1,2,3,4,6,7,8,8a-octahydro-1,2,8,8-tetramethylnaphthalen-2-yl]ethanone (MW=234.38), isobornyl acetate (MW=196.29), alpha-ionone (MW=192.30), beta-ionone (MW=192.30), gamma-ionone (MW=192.30), alpha-damascone (MW=192.30), beta-damascone (MW=192.30), delta-damascone (MW=192.30), 1-(2,4,4-trimethyl-2-cyclohexen-1-yl)-2-buten-1-one (MW=192.30, isodamascone), cedrol (MW=222.40), gamma-dodecalactone (MW=198.30), 2-methyl-3-(3,4-methylenedioxyphenyl)propanal (MW=192.22, Helional) and methyl dihydrojasmonate (MW=226.31).

The molecular weights (MW) and, if appropriate, conventional brand or product names are stated in brackets.

The musk fragrance substance or substances of component (B) (ii) are fragrance substances which have a musk odor. Fragrance substances of this type are known to a person skilled in the art, since musk is a very important odor direction in perfumery. Furthermore, musk fragrance substances, inter alia those mentioned below as being preferred, are described in H. Surburg, J. Panten, "Common Fragrance and Flavor Materials", 5$^{th}$. Edition, Wiley-VCH, Weinheim 2006.

The musk fragrance substance or substances which are part of component (B) (ii) are preferably selected from the group of macrocyclic musk fragrance substances, polycyclic musk fragrance substances and/or alicyclic musk fragrance substances.

Preferred according to the invention are components (B), in particular perfumery fragrance substance mixtures, which comprise two, three or more different musk fragrance substances as component (B) (ii).

In the context of the present invention, the musk fragrance substance or substances of component (B) (ii) are preferably selected from the following Table 1:

TABLE 1

| TYPE | Product/Brand name | Name/CAS Name |
|---|---|---|
| MACRO | EXALTENONE | 4-Cyclopentadecen-1-one (4Z)-; 4-Cyclopentadecen-1-one |
| MACRO | CIVETONE | 9-Cycloheptadecen-1-one, (9Z)- |
| MACRO | CYCLOHEXADECANOLIDE, DIHYDROAMBRETTOLIDE | Oxacycloheptadecan-2-one, ω-Hexadecanolide |
| MACRO | ETHYLENE DODECANDIOATE | 1,4-Dioxacyclohexadecane-5,16-dione |
| MACRO | GLOBALIDE ® | Oxacyclohexadecen-2-one; 15-Pentadec-(11/12)-enolide |
| MACRO | ETHYLENE BRASSYLATE | 1,4-Dioxacycloheptadecane-5,17-dione |
| MACRO | MUSCONE | 3-Methy-cyclopentadecanone |
| MACRO | AMBRETTOLIDE | Oxacycloheptadec-10-en-2-one |
| MACRO | MUSCENONE | 3-Methyl-cyclopentadecenone |
| MACRO | VELVIONE ®, AMBRETONE | 5-Cyclohexadecen-1-one |
| MACRO | AURELIONE ® | 7/8-Cyclohexadecen-1-one |
| MACRO | GLOBANONE ® | 8-Cyclohexadecen-1-one |
| MACRO | ISOMUSCONE ® | Cyclohexadecanone |
| MACRO | EXALTOLIDE, MACROLIDE ® | Oxacyclohexadecan-2-one |
| MACRO | COSMONE ® | 3-Methyl-(5E/Z)-cyclotetradecen-1-one |
| POLY | TRASEOLIDE ® | 1-[2,3-Dihydro-1,1,2,6-tetramethyl-3-(1-methylethyl)-1H-inden-5-yl]-ethanone |
| POLY | PHANTOLIDE ® | 1-(2,3-Dihydro-1,1,2,3,3,6-hexamethyl-1H-inden-5-yl)-ethanone |
| POLY | TONALIDE ® | 1-(5,6,7,8-Tetrahydro-3,5,5,6,8,8-hexamethyl-2-naphthalenyl)-ethanone |
| POLY | CRYSOLIDE | 1-[6-(1,1-Dimethylethyl)-2,3-dihydro-1,1-dimethyl-1H-inden-4-yl]-ethanone |
| POLY | CHROMANOLIDE ® | Tetradecanoic acid, 1-methylethyl ester; Cyclopenta[g]-2-benzopyrane, 1,3,4,6,7,8-hexahydro-4,6,6,7,8,8-hexamethyl- |
| POLY | GALAXOLIDE ® | Cyclopenta[g]-2-benzopyrane, 1,3,4,6,7,8-hexahydro-4,6,6,7,8,8-hexamethyl- |
| ALICYC | HELVETOLIDE ® | 1-Propanol, 2-[1-(3,3-dimethylcyclohexyl)ethoxy]-2-methyl-, 1-propanoate |

MACRO = macrocyclic musk fragrance substances
POLY = polycyclic musk fragrance substances
ALICYC = alicyclic musk fragrance substance Further preferred as part of component (B) (ii) are polycyclic and/or macrocyclic musk fragrance substances, macrocyclic musk fragrance substances in particular having proved to be particularly advantageous in the context of the invention which, in turn, are preferably selected from the group consisting of macrocyclic $C_{14}$-$C_{18}$ ketones and macrocyclic $C_{14}$-$C_{18}$ lactones, the ketone or lactone having a ring size of from 15 to 17 ring atoms and having no oxygen atoms or one or two oxygen atoms in the ring.

Most preferred are 3-methylcyclopentadecenone (Muscenone), 15-pentadec-(11/12)-enolide (Globalide)®, ethylene brassylate, oxacyclohexadecan-2-one (Macrolide®), cyclohexadecanone (Isomuscone®), 8-cyclohexadecanone (Globanone®), (7/8)-cyclohexadecanone (Aurelione®) and mixtures thereof.

In a preferred embodiment, component (B) (ii) is selected from the group consisting of 15-pentadec-(11/12)-enolide (Globalide®), ethylene brassylate and oxacyclohexadecan-2-one (Macrolide®) and mixtures thereof.

The total quantity of the fragrance substance or substances (described as being preferred) of component (B) (ii) (base note) of a composition preferred according to the invention or of a cosmetic product preferred according to the invention is from 5 to 80% by weight, particularly preferably from 10 to 70% by weight, in each case based on the total weight of component (B), preferably based in each case on the total weight of component (B*).

In a composition according to the invention or a cosmetic product according to the invention (in each case particularly in one of the embodiments stated as being preferred), one or more effects are also preferably produced which are selected from the group of effects consisting of:
  reduction of the evaporation of fragrance substances, in particular immediately after application of the composition according to the invention and particularly of the top note and/or base note; this also applies to (readily volatile) fragrance substances which usually fade away shortly after application along with the evaporation of solvents such as ethanol/water;
  temporal stabilization of the odor profile, in other words, a relatively consistent odor profile is achieved over a relatively long period of time;
  increase or temporal stabilization of the olfactory impact (the perceived odor intensity); in other words, the olfactory impact (the perceived odor intensity) is not reduced, or is only negligibly reduced over a long period of time;

prolongation of the adhesion of the fragrance substances of component (B) of a composition according to the invention, in particular of the readily volatile fragrance substances (top note) and/or base note, in turn preferably of component (B) (i) and/or (B) (ii), to skin and/or hair, in particular to human skin, the retention of component (B) of a composition according to the invention or of a cosmetic product according to the invention being longer compared to an otherwise identical composition, or an otherwise identical product, which does not comprise component (A);

imparting of a pleasant feel on the skin of a fragrance substance composition.

The compositions according to the invention are preferably a component of cosmetic products, in particular topical, cosmetic products. With a composition according to the invention or a cosmetic (topical) product according to the invention comprising a sensorially (olfactorily) effective quantity of a composition according to the invention, a prolongation of the adhesion (fixing) of the fragrance substances of component (B) is produced, preferably on skin and/or hair, in particular on human skin. In this respect, one or more further effects which are described in the context of the present invention are preferably achieved, in particular in the embodiments described as being preferred.

The prolonged adhesion (fixing) of the fragrance substances of component (B) was observed particularly in the case of readily volatile fragrance substances (top note) and/or the base note, in turn preferably of component (B) (i) and/or (B) (ii), on skin and/or hair, in particular on human skin, the retention of component (B) of a composition according to the invention or of a cosmetic product according to the invention preferably being at least 10% by weight, preferably at least 15% by weight, more preferably at least 20% by weight greater compared to an otherwise identical composition, or an otherwise identical product, which does not comprise component (A).

In respect of the base note of a composition according to the invention or a cosmetic product according to the invention, in particular in respect of the preferred fragrance substances of component (B) (ii), a greater retention by at least 30% by weight, preferably at least 40% by weight is routinely observed compared to an otherwise identical composition, or an otherwise identical product, which does not comprise component (A).

A composition according to the invention or a (cosmetic) product (particularly in one of the embodiments characterized above as being preferred) comprises in a preferred embodiment, as a further component, an effective quantity of (C) one or more cosmetically acceptable solubilizers for component (B), preferably for component (B*), (B) (i) and/or (B) (ii), preferably selected from the group consisting of (i) ethanol
and
(ii) dipropylene glycol, diethyl phthalate, triethyl citrate, isopropyl myristate and triacetin, with dipropylene glycol being preferred.

Solubilizers according to component (C), in particular the cosmetically acceptable solubilizers stated as being preferred are not regarded as fragrance substances in the context of this specification, in particular not as perfumery fragrance substances. In the context of the present invention, component (C) is not considered as part of component (B) and consequently is not ascribed thereto.

Component (C) is advantageous as a solubilizer for component (B) so that an improved miscibility and (un)mixing stability of component (B) with component (A) is provided, thereby allowing an easier handling and improved further processing, which is advantageous during the preparation of cosmetic products according to the invention.

If a composition according to the invention or a cosmetic product according to the invention comprises a solubilizer according to component (C) which is simultaneously a fragrance substance, this is considered as component (B), in particular for quantitative considerations, and is associated therewith.

If a composition according to the invention or a cosmetic product according to the invention comprises a solubilizer according to component (C) which is simultaneously a diol or triol according to component (D), this is considered as component (D), in particular for quantitative considerations, and is associated therewith.

If a cosmetic product according to the invention comprises component (C) (i) ethanol, the total quantity of component (C) (i) can preferably amount up to 95% by weight of ethanol, preferably at the most 90% by weight, in each case based on the total weight of the product according to the invention.

A composition according to the invention or a cosmetic product according to the invention preferably comprises component (C) (ii) in a total quantity of up to 80% by weight, preferably from 0.5 to 60% by weight, preferably from 1 to 50% by weight, more preferably from 5 to 40% by weight, in each case based on the total weight of component (B).

In an alternative embodiment, a composition according to the invention (particularly in one of the embodiments characterized above as being preferred) comprises as an additional component (D) one or more diols or triols having from 3 to 12 C atoms, preferably selected from the group consisting of glycerin, 1,2-propylene glycol, 1,2-butylene glycol, 1,3-butylene glycol and alkane diols having from 5 to 12 C atoms.

If a composition according to the invention or a cosmetic product according to the invention comprises a diol or triol according to component (D) which is simultaneously a fragrance substance, this is considered as component (D), in particular for quantitative considerations, and is associated therewith. Component (D), in particular the diols and triols stated as being preferred, are not fragrance substances, particularly not perfumery fragrance substances.

If a composition according to the invention or a cosmetic product according to the invention comprises a diol or triol according to component (D) which is simultaneously a solubilizer according to component (C), this is considered as component (D), in particular for quantitative considerations and is associated therewith.

In this respect, the alkane diols having from 5 to 12 C atoms are preferably selected from the group of straight chain 1,2-alkanediols having from 5 to 10 C atoms, in particular from the group consisting of 1,2-pentanediol, 1,2-hexanediol, 1,2-octanediol and/or 1,2-decanediol.

Particularly preferred diols or triols of component (D) are selected from the group consisting of glycerin, 1,2-propylene glycol, 1,2-butylene glycol, 1,3-butylene glycol, 1,2-pentanediol, 1,2-hexanediol, 1,2-octanediol and 1,2-decanediol.

Component (D) can reduce or prevent possible undesirable clouding effects. Furthermore, component (D) can also further improve the adhesion of a composition according to the invention to (human) skin and/or (human) hair, particularly to human skin, and/or the olfactory profile course of a composition according to the invention.

A cosmetic preparation according to the invention preferably comprises component (D) in a total quantity of from 0.2 to 20% by weight, preferably from 0.5 to 10% by weight, more preferably from 1 to 5% by weight, in each case based on the total weight of the cosmetic preparation.

In a composition according to the invention (particularly in one of the embodiments stated above as being preferred), component (D) is preferably present in an effective quantity, i.e. in a quantity in which one or more effects is produced or reinforced by component (D) in the composition, said effects being selected from the group of effects consisting of:
  further reduction of the evaporation of fragrance substances, in particular immediately after application of the composition according to the invention and particularly of the top note and/or the base note;
  a further prolonged adhesion to (human) skin and/or (human) hair, particularly to human skin (this also means human skin but not (oral) mucous membrane), in particular the top note and/or the base note;
  an odor impression which remains the same over a relatively long period of time after application to (human) skin;
  a greater impact following application to (human) skin;
  further temporal stabilization of the odor profile, in other words, an even more consistent odor profile is achieved over a relatively long period of time;
  increase or further temporal stabilization of the olfactory impact (the perceived odor intensity); depending on the respective concentration of component (D) which is used in the composition according to the invention, the impact is increased over a more or less long period of time;
  prolongation of the adhesion of the composition, in particular of the readily volatile fragrance substances (top note), to skin and/or hair, in particular to human skin;
  increase or prolongation of the diffusivity (spatial effect) of the composition, in particular of the readily volatile fragrance substances (top note), to skin and/or hair, in particular to human skin;
  imparting of a further improved pleasant feel on the skin.

A composition according to the invention preferably does not leave a film behind on the skin and/or hair and is thus not perceived as being troublesome. A short time after application (i.e. after drying and, if appropriate, after being absorbed), a composition according to the invention is consistently no longer visible (exception: haircare products such as hair spray, where the formation of a film is desired).

Thus, in short, compositions according to the invention are compositions which have a particularly good adhesion of the top note and/or base note of a fragrance substance composition, a prolonged and/or intensified impact of the top note as well as a prolonged impact of the base note, and a reduction in the heart note preferably cannot be observed or at least can only be observed to a minimal extent.

Further substances which can be part of a (cosmetic) composition according to the invention or of a cosmetic (topical) product according to the invention are as follows:
preservatives, preferably those mentioned in US 2006/0089413, abrasives, anti-acne products and sebum-reducing products, preferably those mentioned in WO 2008/046791, skin anti-ageing products, preferably those mentioned in WO 2005/123101, anti-bacterial agents, anti-cellulite agents, anti-dandruff agents, preferably those mentioned in WO 2008/046795, anti-inflammatory agents, irritation-prevention agents, anti-irritants (anti-inflammatory, irritation-blocking and irritation-preventing agents), preferably those mentioned in WO 2007/042472 and US 2006/0089413, anti-microbial agents, preferably those mentioned in WO 2005/123101, antioxidants, preferably those mentioned in WO 2005/123101, astringents, antiseptic agents, antistatics, binders, buffers, carrier materials, preferably those mentioned in WO 2005/123101, chelating agents, preferably those mentioned in WO 2005/123101, cell stimulants, cleansing agents, conditioning agents, depilatories, surface-active substances, deodorizing agents and antiperspirants, preferably those mentioned in WO 2005/123101, softeners, emulsifiers, preferably those mentioned in WO 2005/123101, enzymes, essential oils, preferably those mentioned in US 2008/0070825, insect repellents, preferably those mentioned in WO 2005/123101, fibers, film formers, further fixatives, foam formers, foam stabilizers, anti-foam substances, foam boosters, fungicides, gelling agents and gel-forming agents, preferably those mentioned in WO 2005/123101, hair care products, hair shaping agents, hair smoothing products, (further) moisture regulators (moisture-releasing substances, moisturizing substances and/or moisture-retaining substances), preferably those mentioned in WO 2005/123101, osmolytes, preferably those mentioned in WO 2005/123101, compatible solutes, preferably those mentioned in WO 01/76572 and WO 02/15686, bleaching agents, starching agents, stain-removing agents, optical brighteners, impregnating agents, dirt-repelling agents, friction-reducing agents, lubricants, moisturizing creams, ointments, opacifiers, plasticizers, covering agents, polish, brighteners, polymers, preferably those mentioned in WO 2008/046676, powders, proteins and protein hydrolyzates, preferably those mentioned in WO 2005/123101 and WO 2008/046676, (further) replumping agents, abrasive agents, skin-calming agents, skin cleansing agents, skin care agents, skin repair agents, preferably comprising cholesterol and/or fatty acids and/or ceramides and/or pseudoceramides, preferably those mentioned in WO 2006/053912, skin brightening agents, preferably those mentioned in WO 2007/110415, skin protection agents, skin softening agents, skin cooling agents, preferably those mentioned in WO 2005/123101, skin warming agents, preferably those mentioned in WO 2005/123101, stabilizers, UV absorbing agents and UV filters, preferably those mentioned in WO 2005/123101, benzylidene-beta-dicarbonyl compounds, preferably those mentioned in WO 2005/107692, alpha-benzoyl cinnamic acid nitriles, preferably those mentioned in WO 2006/015954, AhR receptor antagonists, preferably those mentioned in WO 2007/128723 and WO 2007/060256, detergents, fabric conditioners, suspending agents, skin tanning agents, preferably those mentioned in WO 2006/045760, thickeners, vitamins, preferably those mentioned in WO 2005/123101, oils, waxes and further fats, preferably those mentioned in WO 2005/123101, phospholipids, preferably those mentioned in WO 2005/123101, fatty acids (saturated fatty acids, singly or poly unsaturated fatty acids, α-hydroxy acids, polyhydroxy fatty acids), preferably those mentioned in WO 2005/123101, liquefiers, dyes and color-protecting agents as well as pigments, preferably those mentioned in WO 2005/123101, anti-corrosives, further fragrance substances which are not part of components (B) (i) and (B) (ii), preferably the fragrance substances mentioned in S. Arctander, Perfume and Flavor Chemicals, private publishing house, Montclair, N.J., 1969 and Surburg, Panten, Common Fragrance and Flavor Materials, 5th Edition, Wiley-VCH, Weinheim 2006, in particular the further fragrance substances mentioned explicitly in US 2008/0070825, alcohols and polyols, preferably those mentioned in WO 2005/123101, surfactants, preferably those mentioned in WO 2005/123101, animal extracts, yeast extracts, extracts of algae or microalgae, electrolytes, liquefiers, organic solvents, preferably those mentioned in WO 2005/123101, or silicones and silicone derivatives, preferably those mentioned in WO 2008/046676.

Preferred cosmetic products according to the invention as embodiments of a composition according to the invention are selected from the group consisting of: perfume extracts, eaux de parfum, eaux de toilette, aftershaves, eaux de cologne, pre-shave products, splash colognes and perfumed freshening wipes as well as the perfuming of acidic, alkaline and neutral cleaning compositions, preferably floor cleaners, window cleaners, dishwashing detergents, bath and sanitary cleaners, scouring milk, solid and liquid WC cleaners, pulverulent and foam carpet cleaners, textile fresheners, ironing aids, liquid detergents, pulverulent detergents, laundry pretreatment agents such as bleaches, soaking agents and stain removers, laundry conditioners, laundry soaps, laundry tablets, disinfectants, surface disinfectants and of air fresheners in liquid or gel form or deposited on a solid carrier, aerosol sprays, waxes and polishes such as furniture polishes, floor waxes, shoe creams and bodycare compositions, preferably solid and liquid soaps, shower gels, shampoos, shaving soaps, shaving foams, bath oils, cosmetic emulsions of the oil-in-water, water-in-oil and water-in-oil-in-water types, preferably skin creams and lotions, face creams and lotions, day creams, night creams, sunscreen creams and lotions, aftersun creams and lotions, hand creams and lotions, foot creams and lotions, depilatory creams and lotions, aftershave creams and lotions, tanning creams and lotions, haircare products, preferably hair sprays, hair gels, hairsetting lotions, hair rinses, permanent and semi-permanent hair colorants, hair shaping compositions such as cold waves and hair smoothing compositions, hair tonics, hair creams and lotions, deodorants and antiperspirants, for example underarm sprays, roll-ons, deodorant sticks, deodorant creams, products for decorative cosmetics, preferably eye shadows, nail varnishes, make-up, lipsticks, mascara as well as candles, lamp oils, joss-sticks, insecticides and repellents.

Preferred preparations according to the invention are cosmetic, in particular topical preparations which are composed in the conventional manner and are used for cosmetic light protection, for treating, caring for and cleansing the skin and/or hair or as a make-up product in decorative cosmetics. Accordingly, preparations of this type are present as cleaning agents, preferably as soap, synthetic detergents, liquid wash, shower and bath preparations, haircare products, preferably as emulsion (as solution, dispersion, suspension; cream, lotion or milk depending on the production process and ingredients of the oil-in-water (O/W), water-in-oil (W/O) types or multiple emulsion, PIT emulsion, emulsion foam, micro-, nano-emulsion, pickering emulsion), ointment, paste, gel (including hydro-, hydrodispersion, oleogel), alcoholic or aqueous/alcoholic solution, oil, toner, balsam, serum, powder, wipe, eau de toilette, eau de cologne, perfume, wax, including application as a stick, roll-on, (pump) spray, aerosol (foaming, non-foaming or after-foaming), skincare products (as described above) as foot care products (including keratolytic agents, deodorants), as insect repellents, as sunscreen, as self-tanning agents and/or aftersun preparations, skincare agents as shaving products or after-shave, as depilatories, as haircare products, preferably as shampoo (including shampoo for normal hair, greasy hair, dry, over-processed (damaged) hair, 2-in-1 shampoo, anti-dandruff shampoo, baby shampoo, shampoo for a dry scalp, shampoo concentrate), conditioner, deep conditioner, hair tonic, hair conditioning rinse, hair cream, pomade, perming agents and fixing agents, hair smoothing agents (decurling agents, relaxers), setting lotions, styling aids (preferably gels or waxes), bleaching agents, hair dyes, preferably temporary, direct-acting, semi-permanent hair dyes, permanent hair dyes), skincare products as decorative bodycare products, preferably nail care products (nail varnish and nail varnish remover), decorative cosmetics (for example powder, eye shadow, kohl pencil, lipstick), deodorant and/or antiperspirant.

Cosmetic, preferably topical, preparations according to the invention comprise
component (A) preferably in a quantity of from 0.25 to 30% by weight, preferably from 0.25 to 20% by weight, more preferably from 0.5 to 15% by weight, particularly preferably from 0.5 to 10% by weight and most particularly preferably from 1 to 10% by weight,
and/or
component (B) preferably in a quantity of from 0.15 to 5% by weight, preferably from 0.2 to 3% by weight, more preferably from 0.3 to 3% by weight, particularly preferably from 0.3 to 2.5% by weight and most particularly preferably from 0.3 to 2% by weight,
in each case based on the total weight of the cosmetic preparation.

The compositions according to the invention are preferably so-called "leave-on" products, i.e. products which remain on (human) skin and/or (human) hair and are not usually washed off. A "leave-on" product according to the invention (in a preferred embodiment of a cosmetic product according to the invention) preferably remains for at least 15 minutes or longer, preferably at least at least 30 minutes or longer and more preferably at least at least 60 minutes or longer on (human) skin and/or (human) hair. Included here are in particular eau de partum, eau de toilette, after-shave, (skin) creams, emulsions (for topical application) deodorant sprays, roll-on deodorants, hair sprays, hair conditioner.

Preferred "leave-on" products are selected from the group consisting of:
skin cream or lotion, face cream or lotion, day cream, night cream, sun protection cream, spray or lotion, aftersun cream or lotion, hand cream or lotion, foot cream or lotion, after-shave cream or lotion, skin lightening cream or lotion, skin tanning cream or lotion;
haircare products, preferably hair spray, hair gel, hair-setting lotion, hair tonic, hair cream, hair wax, hair lotion, hair conditioner;
deodorants and antiperspirants, preferably under-arm spray, roll-on, deodorant stick, deodorant cream, and
products for decorative cosmetics, preferably eye shadow, nail varnish, (conditioning) lipstick or mascara.

A composition according to the invention or a cosmetic product according to the invention, preferably in one of the embodiments stated above as being preferred, is preferred which comprises:
(A) cetyl nonanoate and/or stearyl nonanoate in a total quantity of from 0.25 to 30% by weight, preferably from 0.25 to 20% by weight, more preferably from 0.5 to 15% by weight, particularly preferably from 0.5 to 10% by weight and most particularly preferably from 1 to 10% by weight,
and/or
(B) one or more fragrance substances in a quantity of from 0.15 to 5% by weight, preferably from 0.2 to 3% by weight, more preferably from 0.3 to 3% by weight, particularly preferably from 0.3 to 2.5% by weight and most particularly preferably from 0.3 to 2% by weight, wherein preferably component (B) comprises
(B) (i) one, two, three, four, five or more fragrance substances having a molecular weight in the range of from 100 g/mol to 175 g/mol (top note), preferably having a molecular weight in the range of from 110 g/mol to 160 g/mol, preferably in the range of from 115 g/mol to 160 g/mol, particularly preferably in the range of from 120 g/mol to 155 g/mol,
and/or
(B) (ii) one, two, three, four, five or more fragrance substances having a molecular weight of greater than or equal to 190 g/mol (base note), preferably in the range of from 190 g/mol to 300 g/mol, more preferably having a molecular weight in the range of from 195 g/mol to 290 g/mol and most preferably in the range of from 200 to 275 g/mol, and/or (C) (ii) dipropylene glycol, diethyl phthalate, triethyl citrate, isopropyl myristate and triacetin, the total quantity of component (C) (ii) amounting up to 80% by weight, preferably from 0.5 to 60% by weight, preferably from 1 to 50% by weight, more preferably from 5 to 40% by weight, in each case based on the total weight of component (B), and/or (D) one or more diols or triols having from 3 to 12 C atoms, preferably selected from the group consisting of glycerin, 1,2-propylene glycol, 1,2-butylene glycol, 1,3-butylene glycol, 1,2-pentanediol, 1,2-hexanediol, 1,2-octanediol and 1,2-decanediol in a total quantity of from 0.2 to 20% by weight, preferably from 0.5 to 10% by weight, more preferably from 1 to 5% by weight, in each case based on the total weight of the composition or product.

The weight percentages are based in each case on the total weight of the composition. The preferred weight proportions mentioned in respect of components (A), (B), (C) and (D) are preferably adjusted simultaneously.

The present invention also relates to the use of component (A) (as defined above, preferably in an embodiment stated as being particularly preferred) as a means for reducing the evaporation of fragrance substances in a fragrance substance composition, in particular immediately after application;

temporally stabilizing the odor profile of a fragrance substance composition;

increasing or temporally stabilizing the olfactory impact (the perceived odor intensity) of a fragrance substance composition;

prolonging the adhesion of fragrance substances of a fragrance substance composition, in particular the top note and/or base note, to skin and/or hair, in particular to human skin;

and/or imparting or intensifying a pleasant feel on the skin of a fragrance substance composition.

The present invention also relates to a process for reducing the evaporation of fragrance substances in a fragrance substance composition, in particular immediately after application;

temporally stabilizing the odor profile of a fragrance substance composition;

increasing or temporally stabilizing the olfactory impact (the perceived odor intensity) of a fragrance substance composition;

prolonging the adhesion of fragrance substances of a fragrance substance composition, in particular the top note and/or base note, to skin and/or hair, in particular to human skin;

and/or imparting or intensifying a pleasant feel on the skin of a fragrance substance composition, with the following step:

mixing (A) a quantity of cetyl nonanoate and/or stearyl nonanoate which fixes component (B)

and (B) one or more fragrance substances, wherein the mass ratio of component (A) to the total mass of component (B) is preferably in the range of from 1:20 to 200:1, preferably in the range of from 1:12 to 100:1, more preferably in the range of from 1:6 to 50:1, particularly preferably in the range of from 1:5 to 33:1 and most preferably in the range of from 1:2 to 25:1, and optionally further components, preferably selected from the group consisting of components (C) and/or (D) (mentioned above as being preferred), the mass ratio being based on the total weight of the resulting composition after mixing.

The compositions according to the invention can be easily prepared by mixing the individual constituents of components (A) and (B) and optionally (C) and/or (D). In so doing, the sequence of contacting the individual constituents or components is not critical and can be varied.

For the processes according to the invention, the information provided above in respect of preferred compositions according to the invention and cosmetic products applies accordingly.

The present invention also relates to a process for imparting, intensifying or modifying an odor on (human) skin, prolonging the adhesion of fragrance substances of a fragrance substance composition, in particular the top note and/or base note, to skin and/or hair, in particular to human skin, and/or imparting or intensifying a pleasant feel on the skin of a fragrance substance composition, with the following step:

applying a composition according to the invention (preferably a composition which is stated above as being preferred) to (human) skin.

Furthermore, it was found that component (A) is not only suitable as a fixative for fragrance substances, as already described above, but component (A) is also suitable as a solvent for cosmetic UV light protection filters, in particular for lipophilic (crystalline) UV light protection filters. In addition, it was found that due to the uniform distribution of the (preferably lipophilic) cosmetic UV filters, component (A) produces an increase in the SPF, i.e. a higher light protection factor and thus a higher UV protection. In this respect, suitable and preferred UV filters are those mentioned in WO 2005/123101.

In addition, it was found that component (A) improves the gloss of human and animal hair. In this respect, according to one aspect of the present invention, haircare products are preferred, preferably selected from the group consisting of shampoo, in turn preferably shampoo for normal hair, greasy hair, dry, over-processed (damaged) hair, 2-in-1 shampoo, anti-dandruff shampoo, baby shampoo, shampoo for a dry scalp, shampoo concentrate), conditioner, deep conditioner, hair tonic, hair conditioning rinse, hair cream, pomade, perming agents and fixing agents, hair smoothing agents (decurling agents, relaxers), setting lotions, styling aids (preferably gels or waxes); hair dyes.

In addition, it was found that component (A) has a moisture-regulating effect on the skin, in that the skin moisture content of (human) skin is improved and the transepidermal water loss (TEWL) is reduced, without having occluding characteristics.

Further Characteristics of Component (A) in Compositions According to the Invention and Cosmetic Products According to the Invention:

average skin absorption
solid at room temperature (approx. 20° C.)
good (cosmetic) moisturizer
very good replumping characteristics
low polarity noticeably improved feel on the skin provides a water-repelling effect highly resistant to oxidation protects (human) skin from drying out non-occlusive provides a soft, smooth and supple feel on the skin produces a good moisturization, for example as component of deodorants, provides emulsions with consistency and improves their stability.

The following examples illustrate the invention; proportions and percentages relate to the weight, unless indicated otherwise.

EXAMPLES

Abbreviations used: TEA=triethanol amine, SPF=sun protection factor; MW=molecular weight; Ret=retention; DPG=dipropylene glycol In all the following examples, the mixture denoted in the following as "Mixture S" and comprising cetyl nonanoate and stearyl nonanoate was used, which was composed as follows: 67.6% by weight cetyl nonanoate, 27.8% by weight stearyl nonanoate, 2.1% by weight cetyl-2-methyl octanoate, 1.3% by weight myristyl nonanoate, 0.9% stearyl-2-methyl octanoate.

Test 1: Investigation of the Reduced Release of Fragrance Substances from a Fragrance Substance Mixture Comprising 10% by Weight of "Mixture S"

Implementation of Test:

50 µl of a fragrance substance mixture comprising the fragrance substances listed in the following table were dissolved to 0.5% in EtOH. 10% by weight (based on the quantity of perfume oil used) of a mixture comprising cetyl nonanoate and stearyl nonanoate were added to an aliquot of the ethanolic solution.

The two solutions were each applied to a defined surface of smelling strips (2 cm²) and equilibrated for 15 min at 22° C. Thereafter, the smelling strips were each extracted using 4 ml acetone and mixed with 100 µg diphenyl methane as internal standard (IS). The samples were then measured by GC/MS and the amount of fragrance substances remaining on the smelling strips was quantified by the IS method.

The following table shows the results of the quantitative analyses which were carried out and the percentage increase, calculated therefrom, of the retention of the respective perfumery fragrance substance.

| Fragrance substance | MW | GC-Counts with (A) | GC-Counts without (A) | Ret. % | Component | |
|---|---|---|---|---|---|---|
| Melonal | 140.23 | 71121 | 50312 | 41 | (B) (i) | |
| n-Heptanol | 118.23 | 133295 | 65987 | 102 | (B) (i) | |
| Dihydromyrcenol | 156.27 | 329964 | 250262 | 32 | (B) (i) | |
| Camphor | 152.24 | 532089 | 446670 | 19 | (B) (i) | |
| Methyl benzoate | 136.15 | 85111 | 39451 | 116 | (B) (i) | |
| Agrunitrile | 151.25 | 249678 | 95046 | 163 | (B) (i) | |
| Geraniol | 154.25 | 359840 | 211026 | 71 | (B) (i) | |
| 2-Phenylethyl alcohol | 122.17 | 408413 | 317311 | 29 | (B) (i) | |
| Linalool | 154.25 | 213631 | 121770 | 75 | (B) (i) | |
| Anisaldehyde | 136.15 | 440213 | 291215 | 51 | (B) (i) | |
| Vanillin | 152.15 | 251478 | 177240 | 42 | (B) (i) | |
| Isobornyl acetate | 196.29 | 259575 | 75344 | 245 | | (B) (ii) |
| α-Damascone | 192.30 | 384948 | 113119 | 240 | | (B) (ii) |
| β-Ionone | 192.30 | 514323 | 266958 | 93 | | (B) (ii) |
| Lilial | 204.31 | 610208 | 346963 | 76 | | (B) (ii) |
| Cedrol | 222.40 | 812898 | 518214 | 57 | | (B) (ii) |
| γ-Dodecalactone | 198.30 | 615353 | 326625 | 88 | | (B) (ii) |
| Hexyl salicylate | 222.28 | 794870 | 477405 | 66 | | (B) (ii) |
| Helional | 192.22 | 510281 | 328197 | 55 | | (B) (ii) |
| Benzyl benzoate | 212.25 | 843218 | 578062 | 46 | | (B) (ii) |
| ω-Hexadecanolide | 254.40 | 619509 | 421691 | 47 | | (B) (ii) |
| Ethylene brassylate | 270.37 | 651864 | 428545 | 52 | | (B) (ii) |

Melonal = 2,6-dimethyl-5-hepten-1-al;
Helional = 2-methyl-3-(3,4-methylene dioxyphenyl)propanal;
Agrunitrile = 3,7-dimethyl-6-octene-1-nitrile;
Lilial = 2-methyl-3-(4-tert-butylphenyl)propanal.

The results of the quantitative tests clearly demonstrate the fixing characteristics of cetyl nonanoate and stearyl nonanoate. Depending on the respective fragrance substance, it was possible to detect higher quantities in a percentage range of from 19% (camphor) to 240% (alpha-damascone). This clearly shows that the evaporation rate of fragrance substances with a very different chemical structure can be significantly reduced in the presence of a mixture comprising cetyl nonanoate and stearyl nonanoate, as a result of which it was possible to clearly prove the fixing characteristics of these esters for fragrance substances. It was possible to reproduce these analytical results sensorially.

Formulation Examples of Cosmetic Products Comprising a Composition According to the Invention 1=Deodorant stick
2=Shower gel cream
3=Deodorant pump spray
4=Lip care cream with SPF
5=Hand & body lotion
6=Moisturizing cream O/W
7=Sunscreen stick with SPF 50
8=Hair wax
9=Sun protection cream
10=Aftersun spray
11=Day cream
12=Night cream W/O The respective composition of the perfume oils P1 and P2 used in the following cosmetic products 1 to 12 is described further below.

| Material | INCI name | % w/w |  |  |  |  |  |  |  |  |  |  |  |
|---|---|---|---|---|---|---|---|---|---|---|---|---|---|
|  |  | 1 | 2 | 3 | 4 | 5 | 6 | 7 | 8 | 9 | 10 | 11 | 12 |
| "Mixture" |  | 5.0 | 10.0 | 0.5 | 1.0 | 2.5 | 3.0 | 9.0 | 0.5 | 1.5 | 4.0 | 1.0 | 7.0 |
| (−) alpha Bisabolol, natural | Bisabolol |  |  |  |  | 0.1 | 0.1 | 0.1 |  |  |  | 0.2 |  |
| Abil 350 | Dimethicone |  |  |  |  |  | 2.0 |  |  |  |  |  |  |
| Aerosil ® 200 | Silica | 1.5 |  |  |  |  |  |  |  |  |  |  |  |
| Allantoin | Allantoin |  |  |  |  |  |  |  |  |  | 0.1 |  |  |
| Aluminum stearate | Aluminum Stearate |  |  |  |  |  |  |  |  |  |  |  |  |
| Aloe Vera Gel concentrate 10/1 | Aloe Barbadensis Leaf Juice |  |  |  |  |  | 1.0 |  |  |  |  |  |  |
| Avocado oil | Persea Gratissima (Avocado) Oil |  |  |  |  |  |  |  |  |  | 3.0 |  |  |
| Bees wax | Cera Alba |  |  |  | 3.0 |  |  |  |  |  |  |  |  |
| Tert Butyl Hydroxytoluene | BHT |  | 0.1 |  |  |  |  |  |  |  |  |  |  |
| Biotive ® L-Arginine | Arginine |  |  |  |  |  |  |  |  | 0.5 |  |  |  |
| Carbopol ETD 2050 | Carbomer |  |  |  |  |  |  |  |  | 0.3 |  |  |  |
| Carbopol Ultrez-10 | Carbomer |  |  |  |  |  | 0.2 |  |  |  |  | 0.2 |  |
| Carbopol Ultrez-21 | Acrylates/C10-30 Alkyl Acrylate Crosspolymer |  |  |  |  | 0.2 |  |  |  |  |  |  |  |
| Castor oil | Ricinus Communis (Castor) Seed Oil |  | 8.0 |  |  |  |  |  |  |  |  |  |  |
| Citric acid 10% in water | Citric Acid |  | 0.2 |  |  |  |  |  |  |  |  |  |  |
| Corapan TQ | Diethylhexyl 2,6-Naphthalate |  |  |  |  | 2.0 |  |  |  |  |  |  |  |
| Cosmetic color, powder | Color |  |  |  |  |  |  |  |  |  |  | 4.0 |  |
| Covi-Ox T-70 | Tocopherol |  |  |  |  |  |  |  |  |  | 0.1 |  |  |
| Cutina GMS V | Glyceryl Stearate |  |  |  |  | 1.0 | 2.0 |  |  |  |  | 2.5 |  |
| DC 9701 Powder | Dimethicone/Vinyl Dimethicone Crosspolymer |  |  |  |  |  |  | 2.0 |  |  |  |  |  |
| Deolite | Dimethyl Phenylpropanol Pentylene Glycol |  |  | 0.5 |  |  |  |  |  |  |  |  |  |
| Diammonium citrate | Diammonium Citrate |  | 0.1 |  |  |  |  |  |  |  |  |  |  |
| Dow Corning 246 fluid | Cyclohexasiloxane |  |  |  |  |  |  |  |  |  | 2.0 |  |  |
| Dow Corning 345 fluid | Cyclomethicone | Ad 100 |  |  |  | 0.5 |  |  |  |  |  |  |  |
| D-Panthenol 75 L | Panthenol |  | 0.5 |  |  |  |  |  |  |  | 1.0 |  |  |
| Dracorin ® 100 S.E.P. | Glyceryl Stearate, PEG-100 Stearate | 1.0 |  |  |  |  |  |  |  |  |  |  |  |
| Dracorin ® CE | Glyceryl Stearate/Citrate |  |  |  |  |  |  |  |  | 2.0 |  |  |  |
| Dracorin ® GOC | Glyceryl Oleate Citrate Caprylic Capric Triglyceride |  |  |  |  | 2.0 |  | 0.5 |  |  | 2.0 |  |  |
| Drago-Beta-Glucane | Water (Aqua), Butylene Glycol, Glycerin, Avena Sativa (Oat) Kernel Extract |  |  |  |  |  | 1.5 |  |  |  |  | 2.0 |  |
| DragoCalm ® | Water, Glycerin, Avena Sativa (Oat Kernel Extract) |  |  |  | 1.0 |  |  |  |  |  |  |  |  |
| Dragocide ® Liquid | Phenoxyethanol, Methylparaben, Ethylparaben, Butylparaben, Propylparaben, Isobutylparaben |  |  |  |  | 0.8 |  |  |  | 0.8 |  | 0.8 | 0.8 |
| Dragoderm ® | Glycerin, Triticum Vulgare (Wheat) Gluten, Water (Aqua) |  |  |  |  |  |  |  |  |  |  | 2.0 |  |
| Dragosan W/O P | Sorbitan Isostearate, Hydrogenated Castor Oil, Ceresin, Beeswax (Cera alba) |  |  |  |  |  |  |  |  |  |  |  | 8.0 |
| Dragosantol ® 100 | Bisabolol |  | 0.2 |  | 0.1 |  |  |  |  |  |  | 0.2 | 0.2 |
| Dragosine ® | Carnosine |  |  |  |  |  |  |  |  |  | 0.2 |  |  |
| Dragoxat ® 89 | Ethylhexyl Isononanoate |  |  |  |  | 3.0 | 4.0 | 5.0 |  | 3.0 |  | 4.0 | 5.0 |
| EDTA BD | Disodium EDTA |  |  |  |  |  |  |  |  |  | 0.1 | 0.1 |  |
| Emulsiphos ® | Potassium Cetyl Phosphate, Hydrogenated Palm Glycerides |  |  |  |  | 2.5 | 2.0 |  |  |  |  | 2.0 |  |
| Essential oil | Essential Oil |  |  | 3.0 |  |  |  |  |  |  |  |  |  |
| Ethanol | Ethanol |  |  |  | Ad 100 |  |  |  |  |  | 5.0 |  |  |

-continued

| | | % w/w | | | | | | | | | | | |
|---|---|---|---|---|---|---|---|---|---|---|---|---|---|
| Material | INCI name | 1 | 2 | 3 | 4 | 5 | 6 | 7 | 8 | 9 | 10 | 11 | 12 |
| Eusolex T-AVO | Titanium Dioxide, Silica | | | | | | | 5.0 | | | | | |
| Dyes E172 + E171 | Color | | | | | | | 3.0 | | | | | |
| Perfume oil "P1" | Perfume | 1.0 | 2.0 | 3.0 | 0.2 | 0.4 | 0.3 | | | | | | |
| Perfume oil "P2" | Perfume | | | | | | | 0.3 | 0.2 | 0.3 | 0.2 | 0.1 | 0.3 |
| Frescolat ® ML | Menthyl Lactate | | | | | | | | | | 0.5 | | |
| Fruitapone ® Orange B | Propylene Glycol, Water (Aqua), Citric Acid, *Citrus Aurantium* Dulcis (Orange) Juice, Trideceth-9, Bisabolol | | | | | | | | | | 1.0 | | |
| Glycerin 85% in water | Glycerin | | | | | 3.0 | 2.0 | | | | | 3.0 | 3.0 |
| Glycerin | Glycerin | | | | 4.0 | | | | | | 4.0 | | |
| Hydrolite ®-5 | Pentylene Glycol | | | | | 5.0 | 2.0 | | | | 5.0 | | |
| Hydroviton ®-24 | Water, Pentylene Glycol, Glycerin, Lactic Acid, Sodium Lactate, Serine, Urea, Sorbitol, Sodium Chloride, Allantoin | | | | | | 1.0 | | | | | | 2.0 |
| Iso adipate | Diisopropyl Adipate | | | | 0.3 | | | | | | | | |
| Isodragol ® | Triisononanoin | | | | 3.0 | 4.0 | 2.0 | | | | | | |
| Isopropyl palmitate | Isopropyl Palmitate | | | | | | | 13.0 | | | | | |
| Jojoba oil | *Simmondsia Chinensis* (Jojoba) Seed oil | | | | | | | | | | | | 2.0 |
| Keltrol CG RD | Xanthan Gum | | | | 0.4 | 0.1 | 0.1 | | | 0.1 | | 0.1 | |
| Lanette 18 | Stearyl Alcohol | 20.0 | | | | | | | | | | | |
| Lanette E | Sodium Cetearyl Sulfate | | | | 0.75 | | | | | | | | |
| Lanette O | Cetearyl Alcohol | | | | 2.5 | 1.5 | 3.0 | 5.0 | | 2.0 | | 3.0 | |
| Lipex Cocoasoft | *Theobroma Cocoa* Seed Butter | | | | 2.0 | | | | | | | | |
| Mineral oil | Mineral Oil | | | | | | | | 10.5 | | | | 8.0 |
| Neo Heliopan ® 303 | Octocrylene | | | | 7.5 | | | 10.0 | | 5.0 | | | |
| Neo Heliopan ® 357 | Butylmethoxydibenzoyl-methane | | | | | | | 5.0 | | 4.0 | | 1.5 | |
| Neo Heliopan ® AP, 22% in water, neutralized with TEA | Disodium Phenyl Dibenzimidazole Sulfonic Acid | | | | 1.4 | | | | | | | | |
| Neo Heliopan ® E 1000 | Isoamyl p.Methoxycinnamate | | | | 7.5 | | | | | | | 5.0 | |
| Neo Heliopan ® hydro, 25% in water, neutralized with L-arginine | Phenylbenzimidazole Sulfonic Acid | | | | | | | | | 8.0 | | | |
| Neo Heliopan ® hydro, 30% in water, neutralized with TEA | Phenylbenzimidazole Sulfonic Acid | | | | 6.7 | | | | | | | 3.3 | |
| Neo Heliopan ® OS | Ethylhexyl Salicylate | | | | 5.0 | | | | | 5.0 | | | |
| Neutral oil | Caprylic/Capric Triglyceride | | | | | | | Ad 100 | | | 5.0 | | |
| Ozokerite wax 2389 | Ozokerite | | | | | | | | 21.5 | | | | 2.0 |
| PCL Liquid ® 100 | Cetearyl Ethylhexanoate | | | | | 7.0 | 5.0 | | 0.5 | | 4.0 | 5.0 | |
| Pemulen TR-2 | Acrylates/C10-30 Alkyl Acrylate Crosspolymer | | | | | | | | | | 0.3 | | |
| Pluronic ® L-31 | Polaxamer 101 | | 3.0 | | | | | | | | | | |
| Polyglycol 1000 | PEG-20 | 5.0 | | | | | | | | | | | |
| Potassium sorbate | Potassium Sorbate | | | | | 0.1 | | | | | 0.1 | | |
| Propylene glycol | Propylene Glycol | | | 2.0 | | | 3.0 | | | 4.0 | | | |
| Rezal 36 GP | Aluminum Zirconium Tetrachlorohydrex GLY | 10.0 | | | | | | | | | | | |
| Sodium chloride | Sodium Chloride | | | | | | | | | | | | 1.0 |
| NaOH, 10% aqueous solution | Sodium Hydroxide | | | | | 0.5 | 0.6 | | | | | | 0.4 |
| Softisan 100 | Hydrogenated Coco Glycerides | | | | | | | | | | 1.5 | | |
| Solution improver | PEG-40Hydrogenated Castor Oil, Trideceth-9, Propylene Glycol, Water (Aqua) | | | 2.0 | | | | | | | | | |
| Soya bean oil | *Glycine Soya* (Soybean) Oil | | Ad 100 | | | | | | | | | | |
| Squalane, vegetable | Squalane | | | | | | | | | | | 3.0 | |
| Super Hartolan | Lanolin Alcohol | | | | | | | | 0.5 | | | | |
| SymCalmin ® | Pentylene Glycol, Butylene Glycol, Hydroxyphenyl Propamidobenzoic Acid | | | | | | 1.0 | | | | | | |

-continued

| Material | INCI name | % w/w | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| SymClariol ® | Decylene Glycol | 0.3 | | | | | | | | | | | |
| SymDeo ® MPP | Dimethyl Phenylbutanol | 0.5 | | | | | | | | | | | |
| SymDiol ® 68 | 1,2 Hexanediol, Caprylyl Glycol | | | | | 0.5 | | | | | | | |
| SymGlucan ® | Water (Aqua) Glycerin, Beta Glucan | | | | | | | | | | 1.0 | | |
| SymMollient ® W/S | Trideceth-9, PEG-5 Isononanoate | | 1.0 | 0.5 | | | | | | | | | |
| SymRelief ® | Bisabolol, Zingiber Officinale (Ginger) Root Extract | | | | | | | | | | 0.2 | | |
| SymRepair ® | Hexyldecanol, Bisabolol, Cetylhydroxyproline Palmitamide, Stearic Acid, Brassica Campestris (Rapeseed Sterols) | | | | | | 2.0 | | | | 4.0 | | |
| SymVital ™ | Aloe Barbadensis Leaf Juice Powder, Magnesium Ascorbyl Phosphate, Rubus Idaeus (Raspberry) Leaf Extract | | | | | 0.1 | | | | | 0.2 | | |
| Talc | Talc | 1.0 | | | | | | | | | | | |
| TeCE-Ozokerite N502 | Ozokerite | | | | | | | | 23.0 | | | | |
| Tinosorb S ® | Bis-Ethylhexyloxyphenol Methoxyphenyl Triazine | | | | | | | 3.0 | | | | | |
| Triethanolamine (TEA) | Triethanolamine | | | | 0.4 | | | | | | 0.3 | 0.9 | |
| Vaseline | Petrolatum | | | | | | | | | Ad 100 | | | |
| Vitamin E acetate | Tocopherol Acetate | | | | 0.2 | | | 0.7 | | 0.5 | | | 0.2 |
| Wacker Belsil, CDM 3526 VP | C26-C28Alkyl Dimethicone | | | | | | | | 2.0 | | | | |
| Water | Water (Aqua) | | | 10.0 | Ad 100 | Ad 100 | Ad 100 | | | | Ad 100 | Ad 100 | Ad 100 |
| Zetesol 100 | MIPA-Laureth Sulfate, Laureth-4, Cocamide DEA | | 43.0 | | | | | | | | | | |
| Zinc oxide | Zinc Oxide | | | | | 5.0 | | | | | | | |

The perfume oil "P1" with a rose odor used in Formulation Examples 1 to 6 was composed as follows:

| Component/NAME | Parts by weight |
|---|---|
| Acetophenone, 10% in DPG | 10.00 |
| n-Undecanal | 5.00 |
| Gamma-Undecalactone | 15.00 |
| Allyl amyl glycolate, 10% in DPG | 20.00 |
| Amyl salicylate | 25.00 |
| Benzyl acetate | 60.00 |
| Citronellol | 80.00 |
| D-Limonene | 50.00 |
| Decenol trans-9 | 15.00 |
| Dihydromyrcenol | 50.00 |
| Dimethyl benzyl carbinyl acetate | 30.00 |
| Diphenyl oxide | 5.00 |
| GALAXOLIDE ® | 20.00 |
| Geraniol | 40.00 |
| Nerol | 20.00 |
| Geranium oil | 15.00 |
| Hexenol cis-3, 10% in DPG | 5.00 |
| Hexenylsalicylate cis-3 | 20.00 |
| Indol, 10% in DPG | 10.00 |
| Alpha-Ionone | 15.00 |
| Beta-Ionone | 5.00 |
| Lilial ® (2-Methyl-3-(4-tert-butyl-phenyl)propanal) | 60.00 |
| Linalool | 40.00 |
| Methylphenyl acetate | 10.00 |
| Phenylethyl alcohol | 245.00 |
| Styrolyl acetate | 20.00 |
| Terpineol | 30.00 |
| Tetrahydrolinalool | 50.00 |
| Ethylene brassylate | 30.00 |
| Total: | 1,000.00 |

The perfume oil "P2" with a white blossom fragrance and musk note used in Formulation Examples 7 to 12 was composed as follows:

| Component/NAME | Parts by weight |
|---|---|
| Benzyl acetate | 60.00 |
| Citronellyl acetate | 60.00 |
| Cyclamenaldehyde (2-Methyl-3-(4-isopropylphenyl)propanal) | 20.00 |
| Dipropylene glycol | 60.00 |
| Ethyl linalool | 40.00 |
| Florol (2-Isobutyl-4-methyltetrahydro-2H-pyran-4-ol) | 30.00 |
| Globanone [(E/Z)-8-Cyclohexadecen-1-one] | 100.00 |
| Ethylene brassylate | 80.00 |
| Hedione (Methyl dihydrojasmonate) | 140.00 |
| Hexenyl salicylate, cis-3 | 10.00 |

-continued

| Component/NAME | Parts by weight |
|---|---|
| Vertocitral (2,4-dimethyl-3-cyclohexenecarboxaldehyde) | 5.00 |
| Hydratropaaldehyde, 10% in DPG | 5.00 |
| Isodamascone (1-(2,4,4-Trimethyl-2-cyclohexen-1-yl)-2-buten-1-one), 10% in DPG | 5.00 |
| Cyclohexadecanone | 40.00 |
| Jacinthaflor (2-Methyl-4-phenyl-1,3-dioxolane) | 10.00 |
| Cis-Jasmone, 10% in DPG | 20.00 |
| Linalool | 50.00 |
| Linalyl acetate | 30.00 |
| Methyl benzoate, 10% in DPG | 25.00 |
| para-Methylcresol, 10% in DPG | 10.00 |
| Nerol | 20.00 |
| Phenylpropyl aldehyde | 5.00 |
| 2-Phenylethyl alcohol | 82.00 |
| Tetrahydrogeraniol | 13.00 |
| 2,2-Dimethyl-3-cyclohexyl-1-propanol | 40.00 |
| Tonalide ® | 40.00 |
| Total: | 1,000.00 |

The invention claimed is:

1. A composition comprising:
(A) cetyl nonanoate and stearyl nonanoate, wherein the mass ratio of cetyl nonanoate to stearyl nonanoate is from 1:9 to 9:1; and
(B)
(i) one or more fragrance substances having a molecular weight in a range of 100 g/mol to 175 g/mol (top note) selected from the group consisting of n-heptanol, methyl benzoate, agrunitrile, and linalool, and/or
(ii) one or more fragrance substances having a molecular weight of greater than or equal to 190 g/mol (base note) selected from the group consisting of isobornyl acetate, α-damascone, β-ionone, lilial, and γ-dodecalactone,
wherein component (A) is comprised in a fixing quantity for the one or more fragrance substance of component (B), and wherein the mass ratio of component (A) to component (B) is 1:20 to 200:1.

2. The composition as claimed in claim 1 further comprising an effective quantity of:
(C) at least one cosmetically acceptable solubilizer for component (B).

3. The composition as claimed in claim 1 further comprising:
(D) at least one diol or triol having 3 to 12 C atoms.

4. A topical cosmetic product comprising a sensorially effective quantity of the composition as claimed in claim 1.

5. The composition as claimed in claim 1 comprising:
(A) cetyl nonanoate and stearyl nonanoate in a total quantity of 0.25 to 30% by weight of a total weight of the composition,
(B) one or more fragrance substance in a quantity of 0.15 to 5% by weight of the total weight of the composition,
(C) at least one cosmetically acceptable solubilizer selected from the group consisting of dipropylene glycol, diethyl phthalate, triethyl citrate, isopropyl myristate and triacetin, wherein a total quantity of component (C) is 80% or less by weight of a total weight of component (B), and
(D) at least one diol or triol having 3 to 12 C atoms, in a total quantity of 0.2 to 20% by weight of the total weight of the composition.

6. The composition as claimed in claim 1, wherein the mass ratio of component (A) to component (B) is 1:2 to 25:1.

7. The composition as claimed in claim 1, wherein the mass ratio of cetyl nonanoate to stearyl nonanoate is 3:7 to 7:3.

8. The composition as claimed in claim 2, wherein (C) is selected from the group consisting of dipropylene glycol, diethylene phthalate, triethyl citrate, isopropyl myristate and triacetin.

9. The composition as claimed in claim 3, wherein (D) is selected from the group consisting of glycerin, 1,2-propylene glycol, 1,2-butylene glycol, 1,3-butylene glycol, and alkane diols having from 5 to 12 C atoms.

10. The composition as claimed in claim 5, wherein
(A) the total quantity of cetyl nonanoate and stearyl nonanoate is 1 to 10% by weight of the total weight of the composition,
(B) the quantity of the one or more fragrance substance is 0.3 to 2% by weight of the total weight of the composition,
(C) at least one cosmetically acceptable solubilizer selected from the group consisting of dipropylene glycol, diethyl phthalate, triethyl citrate, isopropyl myristate and/or triacetin, wherein a total quantity of component (C) is 80% or less by weight of a total weight of component (B), and
(D) the total quantity of the at least one diol or triol is 1 to 5% by weight of the total weight of the composition.

11. The composition as claimed in claim 1, wherein component (B) comprises:
(B)(i) one or more fragrance substances having a molecular weight in a range of 100 g/mol to 175 g/mol (top note) selected from the group consisting of methyl benzoate and agrunitrile, and/or
(B)(ii) one or more fragrance substances having a molecular weight of greater than or equal to 190 g/mol (base note) selected from the group consisting of isobornyl acetate and α-damascone.

12. A method of prolonging adhesion of a fragrance substance to skin and/or hair comprising applying a composition according to claim 1 to the skin and/or hair.

13. A method of stabilizing an odor profile of a fragrance substance comprising combining:
(A) cetyl nonanoate and stearyl nonanoate, wherein the mass ratio of cetyl nonanoate to stearyl nonanoate is from 1:9 to 9:1; and
(B)
(i) one or more fragrance substances having a molecular weight in a range of 100 g/mol to 175 g/mol (top note) selected from the group consisting of n-heptanol, methyl benzoate, agrunitrile, and linalool, and/or
(ii) one or more fragrance substances having a molecular weight of greater than or equal to 190 g/mol (base note) selected from the group consisting of isobornyl acetate, α-damascone, β-ionone, lilial, and γ-dodecalactone;
wherein the mass ratio of component (A) to component (B) is 1:20 to 200:1.

* * * * *